United States Patent [19]

Schindler

[11] Patent Number: 4,702,917
[45] Date of Patent: Oct. 27, 1987

[54] POROUS BIOABSORBABLE POLYESTERS

[75] Inventor: Anton Schindler, Durham, N.C.

[73] Assignee: Research Triangle Institute, Research Triangle Park, N.C.

[21] Appl. No.: 798,883

[22] Filed: Nov. 18, 1985

[51] Int. Cl.[4] .......................... A61K 9/00; A61L 25/00
[52] U.S. Cl. ...................................... 424/422; 424/423; 424/486; 424/78; 514/953; 514/964; 604/890; 604/891; 264/41; 521/64; 521/182; 523/113
[58] Field of Search ....................... 424/19, 20, 22, 32, 424/78; 514/953, 964, 965; 604/890, 891, 892; 264/41; 523/113; 521/64, 182

[56] References Cited

U.S. PATENT DOCUMENTS

| 3,423,491 | 1/1969 | McLain et al. | 521/64 |
| 3,887,699 | 6/1975 | Yolles | 424/22 |
| 4,076,656 | 2/1978 | White et al. | 521/64 |
| 4,148,871 | 4/1979 | Pitt et al. | 424/22 |

OTHER PUBLICATIONS

Gogolewski et al., "Biodegradable Materials of Polylactides, 4[a)] Porous Biomedical Materials Based on Mixtures of Polylactides and Polyurethanes", Makromol. Chem., Rapid Commun., 3, 839-845, (1982).
Gogolewski et al., "Growth of a Neo-Artery Induced by a Biodegradable Polymeric Vascular Prosthesis", Makromol. Chem., Rapid Commun., 4, 213-219, (1983).
Gegolewski et al., "Resorbable Materials of Poly(-L-Lactide), III, Porous Materials for Medical Application", Colloid and Polymer Sci. 261, 477-484, (1983).

Primary Examiner—John Kight
Assistant Examiner—Nathan M. Nutter
Attorney, Agent, or Firm—Oblon, Fisher, Spivak, McClelland, & Maier

[57] ABSTRACT

Polylactones blended with a polyether and then shaped are leached with aqueous solution of an organic solvent such as alcohol or acetone to elute selectively the polyether and form interconnected pores within the shaped polylactone. The result is a shaped article suitable for use a reservoir for the controlled release of high molecular weight drugs.

19 Claims, 1 Drawing Figure

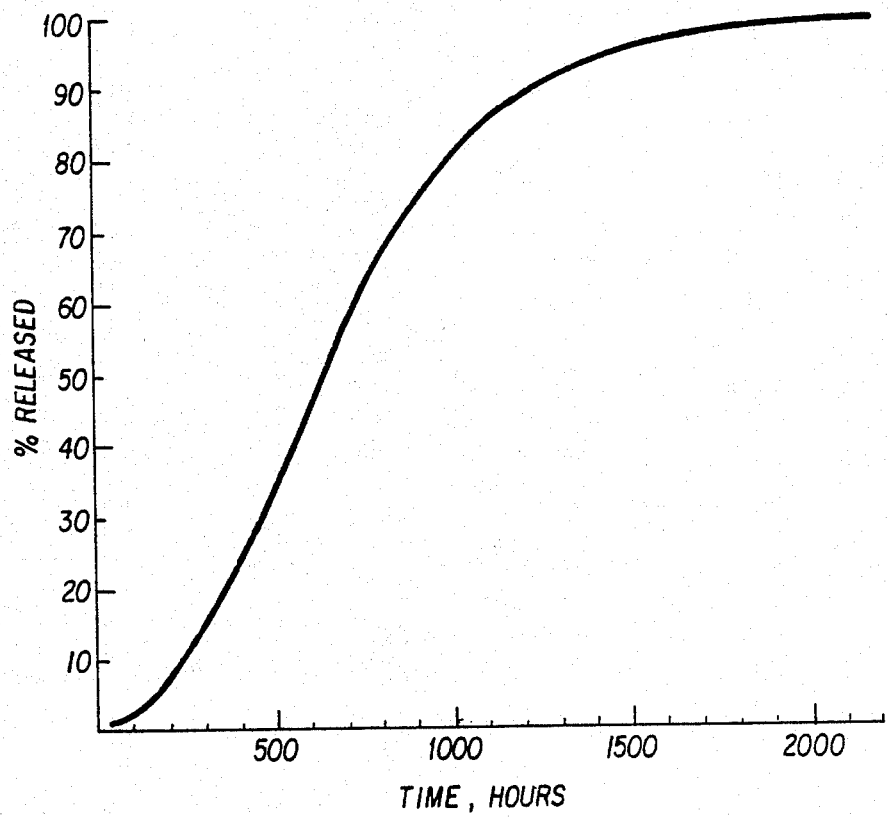

POROUS BIOABSORBABLE POLYESTERS

BACKGROUND OF THE INVENTION

The present invention relates to bioabsorbable polyesters possessing porous structures and their use in novel polymer-drug formulations. More specifically, this invention relates to the frabrication of tubular drug delivery devices from polycaprolactone or its copolymers with other lactones, said devices possessing walls of defined porosities which can be adjusted by proper selection of the production parameters to yield formulations exhibiting the desired rates of drug release.

U.S. Pat. No. 3,887,699 to Yolles discloses a device for dispersing drugs from a biodegradable polymeric material which is shown to be polylactate. U.S. Pat. No. 4,148,871 to Pitt, et al, discloses the use of biodegradable homopolymers and copolymers of ε-caprolactone for formulating devices to accomplish the sustained subdermal delivery of drugs. Neither of these references, however, discloses the use or the fabrication of bioabsorbable devices, exhibiting a porous polymer structure. As a consequence of the dense structure of the polymeric component of the disclosed polymer-drug formulations, the application of these devices is limited to drugs of low molecular weight (less than 500 dalton) which in addition must be sufficiently soluble in the encapsulating polymer. In contrast to both the disclosed drug delivery devices, the novel polymer-drug formulations of the present invention utilize porous polymers and, consequently, the applications of these novel devices are not restricted by the molecular weight of the dispensed drug or its solubility in the polymer.

U.S. Pat. Nos. 4,045,418 and 4,057,537 to Sinclair disclose the fabrications of random copolymers of ε-caprolactone with D,L-lactide and L-lactide, respectively. These patents do not, however, disclose the concept of polymer-drug formulations of the controlled delivery of drugs.

The Netherland Patent Applications Nos. 8202893 and 8202894 to Gogolewski and Pennings disclose the fabrication of porous polyactate and porous polyactate-polyurethane blends and the use of these materials for biodegradable prosthetic devices. the fabrication and the application of porous prosthetic devices derived from polyactate and its blends with polyurethane have been disclosed also in several scientific publications. See for example S. Gogolewski and A. J. Pennings, Makromol. Chem., Rapid. Comm., 3, 839 (1982), 4, 213 (1983); Coll. Polym. Sci., 261, 477 (1983). The disclosures by Gogolewski and Pennings do not include the concept of the controlled release of high molecular weight drugs which is germane to the present invention and are restricted to polylactate and its blends with polyurethanes.

SUMMARY OF THE INVENTION

The controlled release of high molecular weight drugs from polymeric reservoir devices requires porous reservoir walls, epecially for drugs which are hydrophilic and practically insoluble in the hydrophobic polymer. The pores in the reservoir walls have to be interconnected to provide a continuous path for the migrating drug which then diffuses from the reservoir at a rate governed by the tortuosity of the diffusion path.

In accordance with the present invention, tubular devices possessing porous tube walls can be fabricated from polycaprolactone or its copolymers, as well as polyvalerolactone and its copolymers (e.g. with lactic acid) containing an additive which is selectively removed by treatment with appropriate solvents.

Suitable polymers or copolymers have an average molecular weight ranging from about 40,000 to about 250,000 or higher. If the molecular weight is too low, the structure of the device may be too weak and tend to degrade. A preferred average molecular weight is about 100,000.

Pore forming additives of interest are low molecular weight aliphatic polyethers which are commercially available (Pluronics, BASF Wyandotte) so that neither the compounds per se nor the method by which they are obtained constitutes any portion of this invention. Among the different available grades of polyethers, Pluronic F-68 is of particular interest because it has found FDA approval for medical applications. Residues of this polyether remaining in the porous tube walls after the pore-forming process can be tolerated and, indeed, are beneficial for the release performance of the devices by increasing the wettability of the pore surfaces. Appropriate solvents for selectively removing the incorporated polyether from polycaprolactone or its copolymers during the pore forming process are aqueous solutions of organic solvents at concentrations at which dissolution of the polycaprolactone or its copolymers does not take place. Useful solvents for the selective elution of the polyether are among others aqueous solutions of methanol, ethanol, or acetone.

The formation of interconnected pores is demonstrated by the water uptake of the porous polymers. A sample of the porous polymer of known weight is kept submerged in water and the vessel containing the submerged sample is evacuated until gas evolution ceases. Then air is admitted and the sample is weighted after removal of adherent water droplets. The fractional void content, $f_v$, is then calculated from $$f_v = (w_1 + w_2)/w_2$$

where $w_1$ and $w_2$ are the weights of the sample in the dry and wet states, respectively.

Unexpectedly, it was found that the formation of interconnected pores by selective leaching of the pore-forming polyether occurs only inside a narrow temperature range of about 40°–55° C., preferably about 40°–45° C. More specifically, it was found that the leaching temperature and the composition of the eluant play a dominant role which determines the void content and the average pore dimensions of the porous tube walls. This unexpected result which assigns a lesser importance to the initial polyether content is demonstrated by the data of Table 1 which reveal that the void content of the porous polycaprolactone can considerably exceed the volume fraction of the initially present polyether. Indeed, void contents exceeding 60% can be obtained with polycaprolactone initially containing only 5 wt-% of the polyether.

In general the void content increases with the content of the organic component in the aqueous eluant. There exists a critical concentration for the organic component below which the void content remains low despite all of the added polyether beint eluted. For aqueous solutions of acetone this critical concentration is around 45 vol-% acetone at 40° C. elution temperature and decreases to about 25 vol-% acetone at 45° C. Above the critical concentration partial melting and recrystallization of the polycaprolactone takes place during the leaching process which results in a pore structure composed of interconnected pores. Below the critical concentration the porous structure of the leached polycaprolactone changes to one of low void content and being composed of closed cells.

TABLE 1

Effect of Leaching Conditions on the Void Content of the Walls of Porous Polycaprolactone Tubes.

| Vol. % Acetone | Percent Void Content at 40° C. | Content at 45° C. |
| --- | --- | --- |
| Initial F-68 Content: 5 wt % | | |
| 30 | 5.0 | 5.8 |
| 40 | 6.2 | 15.0 |
| 50 | 15.7 | 35.5 |
| 60 | 45.9 | 59.3 |
| 70 | 66.5 | 75.7 |
| Initial F-68 Content: 15 wt % | | |
| 10 | 6.9 | 9.5 |
| 20 | 7.5 | 6.8 |
| 30 | 8.1 | 42.4 |
| 40 | 9.5 | 65.7 |
| 50 | 55.9 | 78.4 |
| 60 | 77.1 | 80.1 |
| Initial F-68 Content: 25 wt % | | |
| 10 | 6.4 | 6.9 |
| 20 | 6.8 | 9.7 |
| 30 | 7.7 | 71.5 |
| 40 | 10.2 | 73.1 |
| 50 | 66.8 | 76.9 |
| 60 | 82.7 | 83.3 |

Broadly stated, the present invention provides an article suitable for use as a controlled release reservoir for high molecular weight drugs, comprising a porous polymer formed by:

(1) shaping a polylactone in the presence of a polyether; and (2) selectively eluting said polyether at a temperature of about 40° C. to 55° C. from said shaped polylactone to form interconnected pores therein.

The invention additionally provides methods for making such an article.

BRIEF DESCRIPTION OF THE DRAWINGS

The FIGURE is a graph which illustrates the cumulative release of decapeptide described in Example 1.

DETAILED DESCRIPTION OF THE INVENTION

The preparation of formulations in which the drug is contained within the cavity of the polymeric device of the present invention is a three step process. The first step involves the preparation of the tubular, non-porous, and drug-free polymeric device suitable for the subsequent pore-forming process. This is accomplished by conventional methods such as extrusion, injection molding, dip casting, or annealing of rolled films utilizing intimate blends composed of polycaprolactone or a suitable copolymer of caprolactone and proper amounts of a polyether such as Pluronic F-68. Intimate blends of polycaprolactone or its copolymers with the pore-forming polyether can also be prepared in situ by polymerizing the corresponding lactones in the presence of the polyether which has to be endcapped by acetyl groups. The amount of polyether such as Pluronic F-68 or its endcapped modification can be in the range of 5–50% (w/w) but is preferentially between 10–25% (w/w).

During the second process step the tube walls are made porous by selectively removing the pore-forming additive in a leaching process utilizing aqueous solutions of an organic solvent such as methanol, ethanol, or acetone. The concentration of the organic component of the leaching bath can be in the range of 10–100% (v/v). The proper selection of the concentration to be utilized depends on the kind of the organic component in the leaching solution, the temperature of the leaching bath, the initial polyether content of the polylactone, and the desired porosity to be obtained in the final product.

The leaching process must be performed at an elevated temperature between about 40° and 55° C. in order to obtain porous tube walls with interconnected pores. During the leaching process the polymer tubes are supported by inserted stainless steel rods and the bath is mildly agitated. Selective elution of the pore-forming additive is generally complete after 2–3 hours when the porous tubes are cooled with ice water to facilitate crystallization. The tubes are then washed with deionized water at ambient temperature, and dried under vacuum at ambient temperature.

In the third step of the process, after frabrication of of the structure, a desired drug is introduced into the cavity of such devices in a suitable form, e.g. as micronized powder or in form of a mixture with a suitable solvent, diluent, or dispersing agent. As is well documented in the public literature, and as is well known to those skilled in the art, the amount of drug, the dimensions of the polymeric device, and the amount of solvent, diluent or dispersing agent, may be varied such that the rate of drug delivery and the time over which the drug is delivered are considered optimum for the particular therapeutic application. The device of the present invention is in the form of a cylindrical tube with the drug contained within the interior cavity formed by the porous walls and both ends of the tubular device being closed by heat sealing.

The rate at which the polymeric device is degraded within the body is determined by the chemical structure and the molecular weight selected for the fabrication of the device as well as the mode of administration to the patient. Polycaprolactone with an intrinsic viscosity in toluene of greater than one dl/g does not begin to lose significant mechanical strength or weight for at least 12 months. A copolymer of caprolactone and dilactide with the same intrinsic viscosity is degraded within two to three months.

The following examples are offered to more fully illustrate the invention, but are not to be construed as limiting the scope thereof.

EXAMPLE 1

A polymer tube of 60 mm length, 2.0 mm innner diameter, and 0.15 mm wall thickness was prepared from a blend composed of 70 parts per weight of polycaprolactone with an intrinsic viscosity of 1.9 dl/g in toluene and 30 parts per weight of Pluronic F-68. After supporting the tube by an inserted stainless steel rod, the Pluronic F-68 was selectively eluted by submerging the tube in a mixture composed of one part ethanol and two parts water at 50° C. for 8 hours. At the end of the leaching period the tube was chilled with ice water, washed, and then dried under vacuum at ambient temperature. From tube weight and geometric dimensions a void content of 59% was calculated. Micrographs obtained by scanning electron microscopy revealed a very open cell structure with interconnected holes in the cell walls of about 6–8 μm in diameter. The pores of the wall surfaces were about 20 μm in diameter and represented about 10% of the tube surface.

A 30 mm length of the prepared porous tube was heat sealed at one end by pressing it under rotation into a fitting conical indentation of a small Teflon block thermostated at 72° C. The tube was then filled with 5.8 mg of a synthetic decapeptide followed by 60 mg of water. After heat sealing the tube was immersed in deionized water at 38° C. and the release of the decapeptide was monitored by its absorbance at 220 nm. The decapeptide was released with a nearly constant rate of 140 μg/day for a time period of 33 days when the device was depleted to about 20% of its initial drug content. The release rate of decapeptide is graphically depicted in the FIGURE.

In a control experiment under identical conditions but utilzing a non-porous polycaprolactone tube of identical dimensions, no release of the decapeptide could be observed during a time period of one month.

EXAMPLE 2

The procedure of example 1 was repeated with incorporation of the following changes. The polymer tube was prepared from a blend composed of 60 parts per weight of the polycaprolactone of example 1 and 40 parts per weight of Pluronic F-68. Selective elution of the Pluronic F-68 content was performed with a mixture of two volumes methanol and three volumes water at 50° C. for 16 hours. The void content of the porous tube walls was found to be 65%.

A porous polymer-drug formulation was prepared by filling a 30 mm length of the prepared porous tube with 4.6 mg of the decapeptide of example 1 and 50 mg of water. The release of the decapeptide into deionized water was monitored as in example 1 for 66 days when the drug content was completely exhausted. The maximum release rate during this time period was found to be 158 μg/day.

EXAMPLE 3

A porous polymer tube was prepared according to the procedure of example 1 but utilizing a methanol-water mixture with a volume ratio of 1:2 for the elution of the Pluronic F-68 content at 50° C. for 10 hours. A 27 mm length of the resulting porous tube was used for the preparation of a polymer-drug formulation composed of 13.4 mg of an oligopeptide with a molecular weight of 5000 and 68 mg of water. The release rate of the oligopeptide into deionized water at 38° C. was monitored for 50 days by its absorbance at 215 nm and was found to be in the range of 20–60 μg/cm/day.

EXAMPLE 4

A porous tube was prepared according to the procedure of example 1 but utilizing a polymer blend composed of 80 parts per weight of polycaprolactone and 20 parts per weight of Pluronic F-68. The Pluronic F-68 content was eluted with a methanol-water mixture of a volume ratio of 2:1 at 50° C. for 1.3 hours. A porous capsule of 27 mm length was prepared which contained 20 mg of riboflavin dispersed in 60 μl of water. The release of the riboflavin into deionized water at 38° C. was monitored by its absorbance at 444 nm. During the investigated time period of 25 days a release rate of 48 μg/cm/day was observed. In a control experiment extending over the same time period the total release of riboflavin from a non-porous polycaprolactone capsule of identical dimensions amounted to less than 5 μg.

EXAMPLE 5

The procedure of example 1 was repeated with incorporation of the following changes. The polymer tube was prepared from a blend composed of 23 parts by weight of Pluronic F-68 and 77 parts per weight of a random copolymer of ε-caprolactone and ε-valerolactone containing 20 mol-% of ester groups derived from the latter lactone. Selective elution of the Pluronic F-68 content was performed at 48° C. in a mixture of equal volumes of methanol and water for 8 hours. The void content of the porous tube wall was found to be 62%.

A 25 mm length of the prepared porous tube was loaded with 5.3 mg of the decapeptide of example 1 and 49 mg of water. The release rate of the decapeptide into deionized water was monitored as in example 1 for 40 days and was found to remain nearly constant at 180 μg/day.

EXAMPLE 6

A porous tube was prepared according to the procedure of example 1 by utilizing a polymer blend composed of 20 parts per weight of Pluronic F-68 and 80 parts per weight of a random copolymer of ε-caprolactone and L-dilactide containing 15 mol-% of ester groups derived from the dilactide. Selective elution of the Pluronic F-68 content at 52° C. in a methanol-water mixture of ratio 3:2 for 6 hours yielded a tube with porous walls with a void content of 78%.

A 30 mm length of the prepared porous tube was loaded with 6.2 mg of the decapeptide of example 1 followed by 70 mg of water. The monitored release rate of the decapeptide into deionized water was found to be 230 μg/day.

EXAMPLE 7

Pluronic F-68 was endcapped with acetyl groups by dissolving 100 g of F-68 in 100 ml freshly distilled pyridine and adding 50 ml freshly distilled acetic anhydride. After refluxing the solution for 6 hours the solvents were removed on a rotary evaporator until solidification. The solid was Soxhlet extracted with pentane for 24 hours and then vacuum dried at 40° C. for 24 hours.

Fifteen parts per weight of the endcapped polyether were dissolved in 85 parts per weight of caprolactone and 200 ppm of stannous octoate were added as a catalyst. The solution was kept in a sealed container at 120° C. for 18 hours when the conversion to polymer was better than 98%. The polymer was removed as a melt from which a film of about 0.1 mm thickness was compression molded. The intrinsic viscosity of the polymer in toluene was 0.7 dl/g.

A porous film was prepared by placing the film into an aqueous solution containing 45 vol-% acetone at 45° C. for 12 hours. The void content of the film as determined by its water uptake was 78%.

EXAMPLE 8

A crosslinked polycaprolactone film was prepared by polymerizing between Teflon plates a solution composed of 85 parts per weight of caprolactone, 15 parts per weight of acetyl endcapped Pluronic F-68 of example 7, 1 part per weight of 2,2-bis(6-hexanolacton-4-yl)propane, and 200 ppm stannous octoate. The polymerization was performed at 120° C. for 18 hours.

The film was made porous by placing it into an aqueous solution containing 70 vol-% acetone at 40° C. for 12 hours. The void content of the crosslinked film as determined by its water uptake was 88%.

While the invention has been described above with reference to specific examples and embodiments, it will be understood that the invention is not to be limited to specific examples and embodiments except as defined in the following claims.

What is claimed is:

1. A article suitable for use as a controlled release reservoir for high molecular weight drugs, comprising a porous polymer formed by
   (a) shaping a polylactone in the presence of a polyether comprised of polyoxypropylene and polyoxyethylene; and
   (b) selectively eluting said polyether with an aqueous solution of an organic solvent from said shaped polylactone at a temperature of about 40° C. to 55° C. to form interconnected pores therein, the resulting pore volume exceeding the amount of material eluted, the resulting product defining a sealed interior reservoir in communication with said pores, which reservoir is suitable to receive said drugs.

2. The article of claim 1 wherein said polyether is endcapped with acetyl groups.

3. The article of claim 1 wherein the endcapped polyether of claim 2 is added to the monomeric lactone prior to the polymerization.

4. The article of claim 1 wherein, prior to said selective elution step, said polyether is present in an amount of 5-50% based on the weight of said blend.

5. The article of claim 4 wherein said polyether is present in an amount of 10-30% based on the weight of said blend.

6. The article of claim 1, wherein said polylactone is polycaprolactone.

7. The article of claim 1, wherein said polylactone is a copolymer formed from caprolactone and at least one other lactone or bis-lactone.

8. The article of claim 1, wherein said shaped polylactone is in the form of a tube.

9. The article of claim 1, wherein said organic solvent is acetone present in an amount of 20-70%.

10. The article of claim 1, wherein said organic solvent is methanol or ethanol present in an amount of 20-50%.

11. A method of fabricating a porous shaped article suitable for use as a controlled release reservoir for high molecular weight drugs, comprising:
    (a) shaping a blend of a polylactone and polyether comprised of polyoxypropylene and polyoxyethylene to form a shaped article; and
    (b) selectively eluting said polyether from said shaped article with an aqueous solution of an organic solvent to form interconnected pores therein, said elution step being conducted under temperature conditions such that the resulting pore volume is greater than the amount of material eluted.

12. The method of claim 11 wherein said polyether is endcapped with acetyl groups and is added to the monomeric lactone prior to the polymerization.

13. The method of claim 12, wherein prior to said selective elution step, said polyether is present in an amount of 5-50% based on the weight of said blend.

14. The method of claim 13, wherein said polyether is present in an amount of 10-30% based on the weight of said blend.

15. The method of claim 12, wherein said polylactone is polycaprolactone.

16. The method of claim 12, wherein said polylactone is a copolymer formed from caprolactone and at least one other lactone or bis-lactone.

17. The method of claim 12, wherein said shaped polylactone is in the form of a tube.

18. The method of claim 12, wherein said organic solvent is acetone present in an amount of 20-70%.

19. The method of claim 12, wherein said organic solvent is methanol or ethanol present in an amount of 20-50%.

* * * * *